United States Patent
Iwata

(10) Patent No.: US 7,574,901 B2
(45) Date of Patent: Aug. 18, 2009

(54) FLOW PATH SWITCHING VALVE, HIGH PERFORMANCE LIQUID CHROMATOGRAPHY USING THE SAME AND ANALYTICAL METHOD THEREOF

(75) Inventor: Yosuke Iwata, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 61 days.

(21) Appl. No.: 11/733,957

(22) Filed: Apr. 11, 2007

(65) Prior Publication Data
US 2007/0251302 A1 Nov. 1, 2007

(30) Foreign Application Priority Data
Apr. 26, 2006 (JP) ............... 2006-121389

(51) Int. Cl.
*G01N 1/00* (2006.01)
*F16K 11/074* (2006.01)
(52) U.S. Cl. ................. 73/61.56; 137/625.46
(58) Field of Classification Search ........... 73/61.56; 137/625.15, 625.19, 25.416, 137.46, 625.17
See application file for complete search history.

(56) References Cited

U.S. PATENT DOCUMENTS

| | | | | |
|---|---|---|---|---|
| 3,477,207 A * | 11/1969 | Auger | ............. | 96/104 |
| 3,748,833 A * | 7/1973 | Karas et al. | ............. | 96/105 |
| 3,796,232 A * | 3/1974 | Dalton | ............. | 137/625.21 |
| 3,868,970 A * | 3/1975 | Ayers et al. | ............. | 137/625.46 |
| 4,614,204 A * | 9/1986 | Dolejs | ............. | 137/625.11 |
| 4,625,569 A * | 12/1986 | Toei et al. | ............. | 73/863.72 |
| 4,632,149 A * | 12/1986 | Oroskar et al. | ............. | 137/625.15 |
| 4,633,904 A * | 1/1987 | Schumann et al. | ............. | 137/625.15 |
| 5,010,921 A * | 4/1991 | Nohl | ............. | 137/625.46 |
| 5,105,851 A * | 4/1992 | Fogelman | ............. | 137/625.11 |
| 6,012,487 A * | 1/2000 | Hauck | ............. | 137/625.11 |
| 6,161,583 A * | 12/2000 | Morris | ............. | 137/625.21 |
| 6,672,336 B2 * | 1/2004 | Nichols | ............. | 137/625.46 |
| 6,789,573 B2 * | 9/2004 | Knapp | ............. | 137/625.15 |
| 6,874,354 B2 * | 4/2005 | Cueni et al. | ............. | 73/61.55 |
| 6,997,213 B1 * | 2/2006 | Towler et al. | ............. | 137/625.46 |
| 7,213,615 B2 * | 5/2007 | Cueni et al. | ............. | 137/625.46 |

FOREIGN PATENT DOCUMENTS

| | | |
|---|---|---|
| CN | 1327157 A | 12/2001 |
| JP | 62056858 A * | 3/1987 |
| WO | WO 2004088303 A1 * | 10/2004 |

* cited by examiner

*Primary Examiner*—John Fitzgerald
(74) *Attorney, Agent, or Firm*—J.C. Patents

(57) ABSTRACT

A flow path switching valve is provided, in which an impact due to the pressure change when a flow path is switched is prevented from being generated. (A) A rotor slot 1c allows an analysis infusion pump 11 to be connected to an analytical column 13, so as to form a flow path (condensing procedure). (B) The rotor of the flow path switching valve 1 is rotated clockwise for 30 degrees, the rotor slot 1c allows the analysis infusion pump 11, the analytical column 13, and a trap column 5 be connected. After the pressure in the trap column 5 is raised to the same pressure level as that of the analytical column 13, the pressure is stabilized, and the pressure difference between the two columns 5 and 13 is counteracted (high-pressure procedure). (C) After the pressure between the two columns 5 and 13 has been stabilized sufficiently, the rotor is further rotated for 30 degrees, and the trap column 5 and the analytical column 13 are connected in series, so the sample analysis can be performed (dissolution procedure and detection procedure).

7 Claims, 3 Drawing Sheets

FLOW PATH SWITCHING VALVE, HIGH PERFORMANCE LIQUID CHROMATOGRAPHY USING THE SAME AND ANALYTICAL METHOD THEREOF

CROSS-REFERENCE TO RELATED APPLICATION

This application claims the priority benefit of Japanese application serial no. 2006-121389, filed Apr. 26, 2006. All disclosure of the Japanese application is incorporated herein by reference.

BACKGROUND OF THE INVENTION

1. Field of the Invention

The present invention relates to a high performance liquid chromatography for separating and analyzing the various compounds in a sample, and an analytical method of the same, and a flow path switching valve used by the same.

2. Description of Related Art

As for mass spectrometers used for determining the structures of proteins or peptides in the field of life science, in order to optimize the sensitivity, it is required to minimize the flow in the high performance liquid chromatograph (HPLC) served as the previous stage of a mass spectrometer.

Generally, the HPLC employed in an ordinary analysis is operated by feeding a liquid as a mobile phase at a flow rate of about 1 mL/min into a column with an inner diameter of about 4.6 mm. However, as for mass spectrometers, Micro-HPLCs for feeding a liquid at a flow rate of about 5 µL/min into a column with an inner diameter of about 0.3 mm have been gradually applied. In addition, Nano-HPLCs for feeding a liquid as the mobile phase at a flow rate of about 200 nL/min into a column with an inner diameter of 0.075 mm have been gradually commercialized.

When the extremely low-flow HPLCs are used for analysis, the sample may be diffused due to the volume (about 100 µL) in the system, thus affecting the sensitivity of the mass spectrometer. Therefore, after the sample is injected into the system with an auto-injector or a manual injector, the sample is adsorbed in a trap column, connected to the flow path switching valve, for being condensed. Then, the flow path switching valve is switched to feed the mobile phase liquid used for analysis into the trap column, so that the sample adsorbed on the trap column is removed from the trap column, and then separated through an analytical column in a latter stage. Finally, the mass of the sample is analyzed by a mass spectrometer.

The flow path switching valve employed in an extremely low-flow HPLC has a small inner volume due to the same reason as that mentioned above. Generally, the main components of a flow path switching valve include a housing cover for fixing the pipes of the flow path switching valve, a rotor for switching flow paths through rotation, and a stator, disposed between the housing cover and the rotor, for keeping liquid-tightness. In the extremely low-flow HPLC, the flow path switching valve with a stator and a housing cover being integrated as a whole is generally used, so as to reduce the inner volume of the valve.

FIGS. 3A-3B are a flow path diagram of an HPLC using a flow path switching valve in the conventional art, in which FIG. 3A shows the flow path when the sample is condensed; and FIG. 3B shows the flow path when the sample is analyzed.

Each port of the flow path switching valve 21 is respectively connected through the flow paths to a trap column 5 for condensing the sample, a sample injection portion 9 for injecting the sample into the flow path between a pump 7 and the trap column 5, an analysis infusion pump 11 for feeding the mobile phase liquid used for the analysis in order to separate the ingredients already condensed by the trap column 5, and an analytical column 13 for separating the ingredients already condensed by the trap column 5. The analytical column 13 includes a detector 14 connected thereto in the downstream.

On the rotor of the flow path switching valve 21, three circular rotor slots 21a-21c are formed, as shown in FIGS. 3A and 3B. By means of rotating the rotor for 60 degrees, the combination of the rotor slots and the corresponding ports can be switched, so that the sample condensation and the sample separation and analysis can be performed.

SUMMARY OF THE INVENTION

In the flow path switching valve 21, the pipe used for connecting the trap column 5 to the valve 21 may have an inner diameter of 25 µm and a length of about 50 mm. If the volumes of the inlet and the outlet are also considered, the volume of the pipe is about 50 nL.

In addition, the pitch circle of the rotor slots 21a-21c has a radius of 5 mm, a width of 0.1 mm, and a depth of about 0.1 mm, and the volume of the rotor slot is 10 nL. Furthermore, the flow path of the stator has an inner diameter of 0.1 mm, a length of 1 mm, and a volume of 15 nL. Therefore, the inner volume between two ports is 25 nL, and added with the volume (50 nL) of the pipe, the volume becomes about 75 nL.

Moreover, the trap column 5 uses a packed column with an inner diameter of 200 µm and a length of about 30 mm, and the total volume of the system volume (75 nL) and the volume of the trap column is about 1 µL.

As shown in FIG. 3A, when the sample is condensed, the internal pressure of the trap column 5 is about 1 MPa. However, under the circumstance of using a Nano-LC for analysis, after the liquid has been fed by the analysis infusion pump 11, the pressure applied to the analytical column 13 is about 5 MPa.

As shown in FIG. 3B, after the sample has been condensed and when the flow path switching valve 21 is switched to analyze the sample, due to the pressure (1 MPa) in the trap column, the pressure (5 MPa) in the analysis infusion pump 11 is reduced sharply.

At this time, due to the switching impact of the flow path switching valve 21, the pressure in the analytical column 13 is reduced sharply, so that feeding the mobile phase liquid from the analysis infusion pump 11 becomes not fluent, which influences the reproducibility of the retention time.

Accordingly, the present invention is directed to a flow path switching valve, which will not generate an impact due to the pressure change when the flow path is switched, and also directed to an HPLC using the flow path switching valve.

As embodied and broadly described herein, the present invention provides a flow path switching valve for switching ports connected to rotor slots by rotating a rotor having a plurality of rotor slots formed thereon. The flow path switching valve is characterized in that, one of the rotor slots is a long rotor slot with a length sufficient for connecting three ports at the same time, and the rotor is switched between one position, at which the long rotor slot connects three ports, and the other position, at which the long rotor slot connects merely two ports.

The HPLC of the present invention includes: a trap column, for condensing the sample; a condensation infusion pump, for feeding the mobile phase liquid used for condensation into the trap column; a sample injection portion, disposed on the flow path between the condensate infusion pump and the trap column, for injecting the sample into the mobile phase liquid used for condensation; an analytical column, for separating the ingredients of the sample; an analysis infusion pump, for feeding the ingredients already condensed by the trap column into the analytical column by using the mobile phase used for the analysis; and a detector, for performing a separation with the analytical column and detecting the dissolved ingredients. In addition, the trap column, the analysis infusion pump, and the analytical column are arranged adjacent to one another in the following manner: connected to three ports of the flow path switching valve of the present invention, and the port of the trap column and the port of the analytical column are respectively located at two sides of the port of the analysis infusion pump. Through the rotation of the rotor, the following connections achieved by the long rotor slot can be interchanged, i.e., a connection between the trap column, the analysis infusion pump, and the analytical column, a connection between the analysis infusion pump and the trap column, and a connection between the analysis infusion pump and the analytical column.

A high pressure is required when the separation is performed by an analytical column; and the liquid-feeding pressure of the analysis infusion pump is higher than that of the condensation infusion pump.

The HPLC analytical method of the present invention adopts the HPLC of the present invention, and includes the following procedures (A)-(E) successively.

(A) Condensation procedure, in which the rotation angle of the rotor is served as an angle at which the flow path from the sample injection portion is connected to the trap column, and the sample is led into the trap column, so as to condense the ingredients in the sample;

(B) High-pressure procedure, in which the rotation angle of the rotor is served as an angle at which the trap column, the analysis infusion pump, and the analytical column are connected through the long rotor slot, so as to eliminate the pressure difference between the trap column and the analytical column;

(C) Dissolution procedure, in which the rotation angle of the rotor is served as an angle at which the analysis infusion pump is connected to the trap column through the long rotor slot and the trap column is connected to the analytical column through other rotor slots, so as to dissolve the ingredients already condensed in the trap column;

(D) Separation procedure, in which the rotation angle of the rotor is served as an angle at which the analysis infusion pump is connected to the analytical column, and the ingredients already dissolved from the trap column are separated by the analytical column; and (E) Detection procedure, in which the ingredients already dissolved from the analytical column are detected by a detector.

[Efficacy of the Invention]

The rotor slot has a long rotor slot with a length sufficient for connecting three ports at the same time, and the rotor is interchanged between one position, at which the long rotor slot connects three ports, and the other position, at which the long rotor slot connects merely two ports. Therefore, the pressure difference generated among the three ports can be counteracted.

The analysis infusion pump is arranged adjacent to the trap column and the analytical column, in the manner of connecting concurrently, through the long rotor slot, the port of the analysis infusion pump to the port of the trap column and to the port of the analytical column. Therefore, the state of counteracting the pressure difference between the trap column and the analytical column can be achieved, and that the mobile phase liquid can be fluently fed from the analysis to achieve a high reproducibility of the retention time.

The following procedures are performed: performing a condensation procedure to lead the sample into the trap column and to condense the ingredients in the sample; performing a high-pressure procedure to eliminate the pressure difference between the trap column and the analytical column; performing a dissolution procedure to connect the analysis infusion pump and the trap column and to dissolve the ingredients already condensed by the trap column; performing a separation procedure to separate the ingredients already dissolved from the trap column by using the analytical column; and performing a detection procedure to detect the ingredients already dissolved from the analytical column by using a detector. Therefore, the mobile phase liquid can be fluently fed from the analysis infusion pump, so as to achieve a high reproducibility of the retention time.

In order to provide the aforementioned and other aspects, features, and advantages of the present invention be more comprehensible, preferred embodiments accompanied with figures are described in detail below.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIGS. 1A-1D show an embodiment of a flow path switching valve, in which FIG. 1A is a perspective view, FIG. 1B is a plan view of a housing cover; FIG. 1C is a plan view of a rotor; and FIG. 1D is a sectional view of FIG. 1B taken along the line of X-X'.

FIGS. 2A-2C are flow path diagrams of an HPLC according to an embodiment of the present invention, in which FIG. 2A shows the flow path when the sample is condensed; FIG. 2B shows the flow path when the pressure difference is counteracted; and FIG. 2C shows the flow path when the sample is separated and detected.

FIGS. 3A-3B show flow path diagrams of an HPLC using a flow path switching valve in the conventional art, in which FIG. 3A shows the flow path of the HPLC when the sample is condensed; and FIG. 3B shows the flow path of the HPLC when the sample is analyzed.

DESCRIPTION OF EMBODIMENTS

Figure 1:
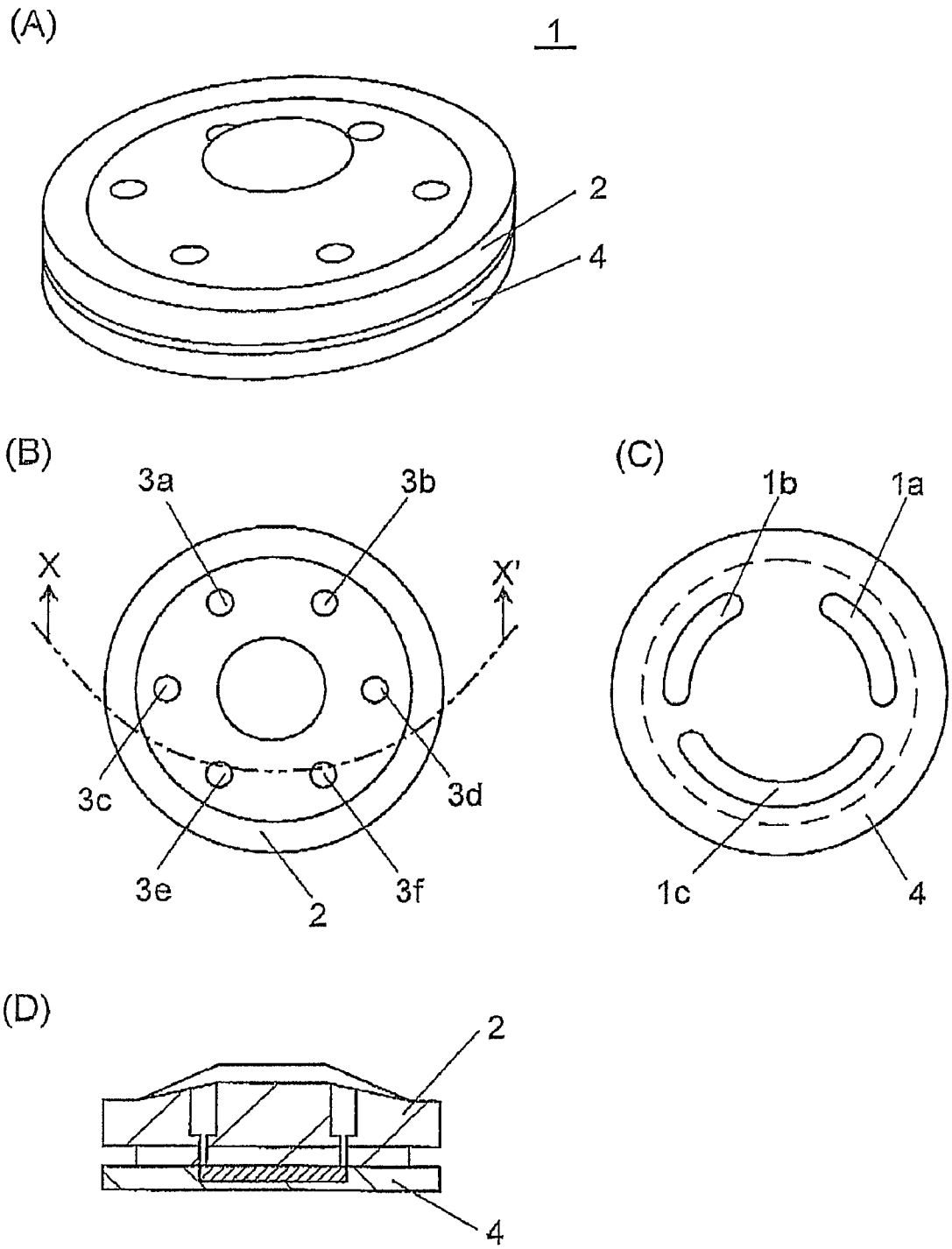

Hereinafter, an embodiment of the present invention is described below in detail.

FIGS. 1A-1D show a flow path switching valve, in which FIG. 1A is a perspective view, FIG. 1B is a plan view of a housing cover, FIG. 1C is a plan view of a rotor, and FIG. 1D is a vertical sectional view of FIG. 1B taken along the line of X-X'. The flow path switching valve 1 is formed by a rotor 4 and a housing cover 2, the rotor 4 is a rotor for switching the flow path, and the housing top 2 also functions as a stator for maintaining liquid-tightness of the rotor 4 during rotating. In this embodiment, in order to reduce the volume in the valve 1, the housing cover 2 can also serve as a stator.

On the housing cover 2, six ports 3a-3f are disposed for being connected to external flow paths, and the ports 3a and 3b are respectively an IN port and an OUT port facing the trap column, the port 3c is a port for connecting the mobile phase liquid used for condensing, the port 3d is a port for connecting a liquid outlet, and the ports 3e and 3f are respectively an IN port and an OUT port of the mobile phase liquid used for the analysis.

On the surface of the rotor 4 that faces the housing top 2, circular rotor slots 1a and 1b connected between two ports, and a circular long rotor slot 1c connected among three ports are formed. One pitch circle formed by the rotor slots 1a and 1b has, for example, a radius of 2.5 mm, an inner angle of 60 degrees, a width of 0.1 mm, a depth of about 0.1 mm, and a volume of about 40 nL. The pitch circle of the long rotor slot 1c has, for example, a radius of 2.5 mm, an inner angle of 120 degrees, a width of 0.1 mm, a depth of about 0.1 mm, and a volume of about 40 nL. The rotor slots 1a-1c can be formed, for example, by mechanical processing.

Hereinafter, the embodiment is described below.

The rotor slots 1a and 1b of the rotor 4 are formed by rotating from the central axis for 60 degrees, respectively. Therefore, when the rotor slots 1a and 1b are connected to the ports to form flow paths, the combination of the rotor slots 1a-1c and the ports 3a-3f can be switched by rotating the rotor 4 for 60 degrees.

For example, the rotor slot 1a is located between the ports 3b and 3d, the rotor slot 1b is located between the ports 3a and 3c, and the long rotor slot 1c is located between the ports 3e and 3f. Under this condition, if the rotor 4 is rotated clockwise for 60 degrees, the rotor slot 1b is located between the ports 3a and 3b, the rotor slot 1a is located between the ports 3d and 3f, and the long rotor slot 1c is located between the ports 3c and 3e.

In addition, the long rotor slot 1c is formed under a rotation angle of 120 degrees; thus, three ports formed under a rotation angle of 60 degrees can be connected at the same time.

For example, the rotor slot 1a is located between the ports 3b and 3d, the rotor slot 1b is located between the ports 3a and 3c, and the long rotor slot 1c is located between the ports 3e and 3f. Under this condition, if the rotor 4 is rotated clockwise for 30 degrees, the long rotor slot 1c is located among the ports 3c, 3e, and 3f, the port 3d is located in the rotor slot 1a, and the port 3a is located in the rotor slot 1b, while the port 3b is not located in any rotor slot.

Figure 2:
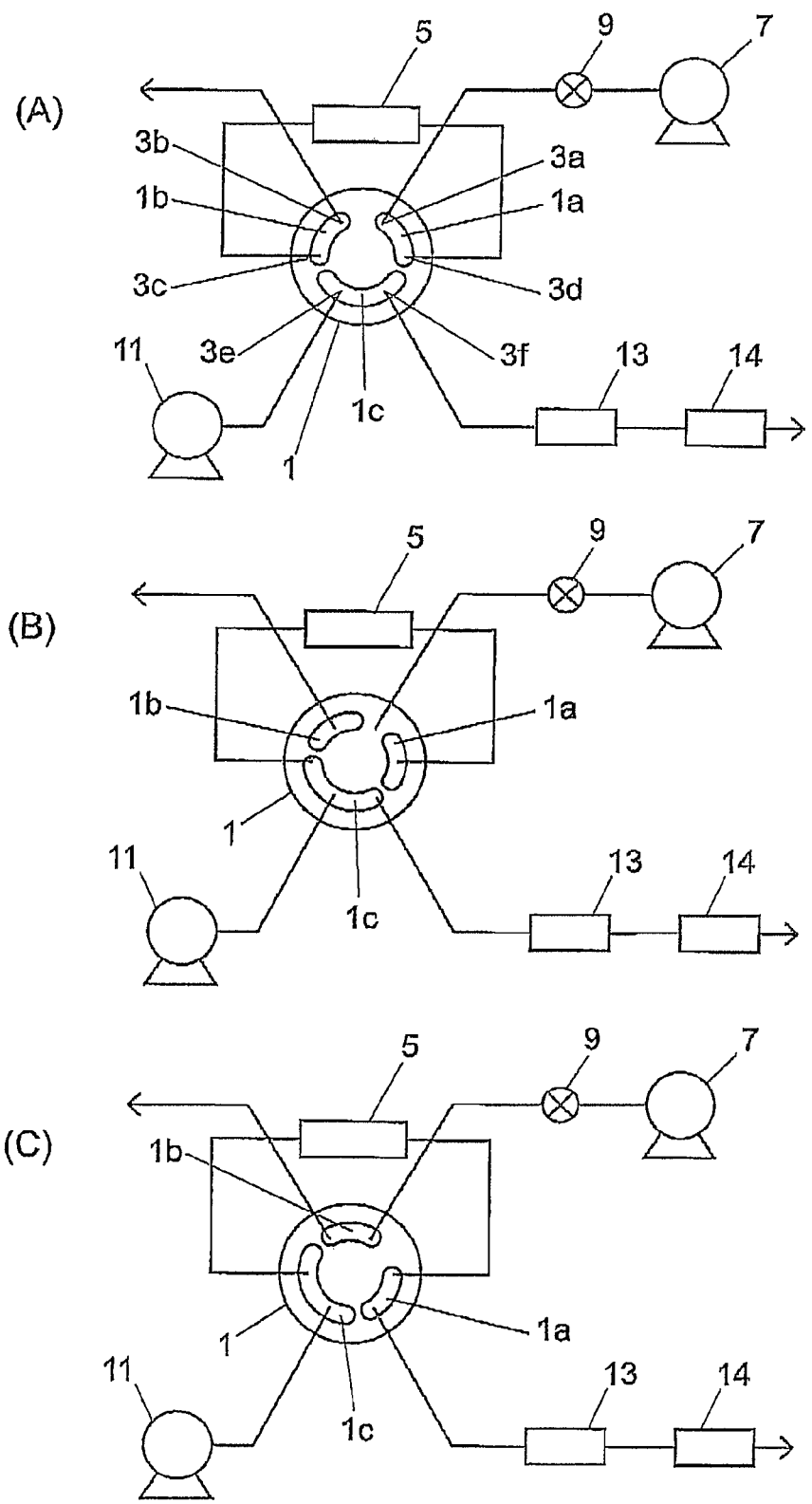
Figure 3:
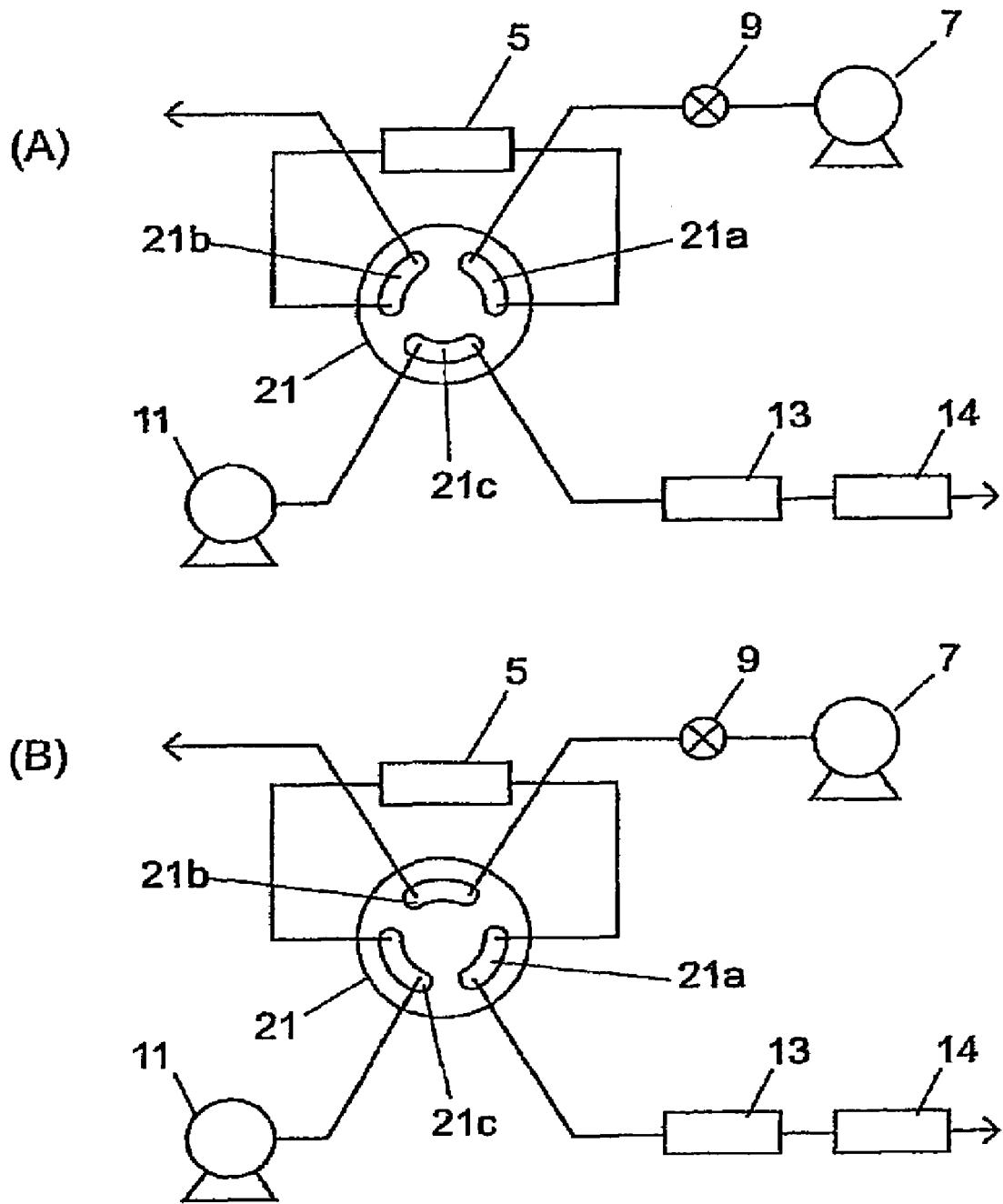

FIGS. 2A-2C show a flow path of an HPLC according to an embodiment of the present invention, in which FIG. 2A shows a condensation procedure, FIG. 2B shows a high-pressure procedure, and FIG. 2C shows a dissolution procedure and a separation, detection procedure.

Each port (3a-3f) of the flow path switching valve 1 is respectively connected through the flow path to: a trap column 5 for condensing the sample, a sample injection portion 9 for injecting the sample into the flow path between the condensing pump 7 and the trap column 5, an analysis infusion pump 11 for feeding liquid in order to separate the ingredients already condensed by the trap column 5 by means of a mobile phase used for the analysis, an analytical column 13 for detecting the ingredients separated in the trap column 5, and a liquid outlet. The analytical column 13 includes a detector 14 connected thereto in the downstream.

As shown in FIG. 1, the rotor of the flow path switching valve 1 has three circular rotor slots (1a-1c) formed thereon, so that the combination of the rotor slot and the corresponding port can be switched by rotating the rotor.

The rotor slot is formed through the following manners, i.e., the inner angles of the two rotor slots (1a, 1b) are 60 degrees, and the inner angle of the long rotor slot 1c is 120 degrees.

(A) When the sample is condensed, the long rotor slot 1c allows the analysis infusion pump 11 be connected with the analytical column 13 to form a flow path, and allows the rotor slots 1a, 1b, the condensation pump 7, the sample injection portion 9, the trap column 5, and the liquid outlet be connected to form a flow path. In this way, the sample fed from the sample injection portion 9 is condensed in the trap column 5, and the mobile phase used for condensation is discharged via the liquid outlet.

(B) After the sample has been condensed, the rotor of the flow path switching valve 1 is rotated clockwise for 30 degrees, and the long rotor slot 1c allows the analysis infusion pump 11, the analytical column 13, and the trap column 5 be connected. The port 3d on the other end of the trap column 5 is connected with the rotor slot 1a. However, the rotor slot 1a is not connected with other flow paths, so the mobile phase liquid used for the analysis dose not flow through the trap column 5.

In addition, the port 3a connected to the condensing pump 7 is not connected with any rotor slot. Therefore, before rotating the rotor of the flow path switching valve 1, the flow rate of the condensation pump must be set to be 0 mL/min. Thus, after the pressure of the trap column 5 is raised to the same pressure level as the analytical column 13, the pressure is stabilized, so that the pressure difference between the two columns 5 and 13 is counteracted.

(C) After the pressure difference between the two columns 5 and 13 is stabilized, the rotor is further rotated clockwise for 30 degrees, such that the trap column 5 and the analytical column 13 are connected in series, and then, the sample already condensed in the trap column is separated by the analytical column 13. At this time, since no pressure impact is generated in the analysis infusion pump 11, the mobile phase liquid used for the analysis can be fed fluently, so as to ensure a desirable reproduction of the retention time of the sample.

In order to measure and determine the pressure difference between the two columns 5 and 13, a pressure meter can be disposed in the flow path for connecting the two columns 5 and 13.

Afterwards, the ingredients dissolved from the analytical column 13 are detected by the detector 14.

In addition, if the flow rate is 1 mL/min, which is generally used in the HPLC, the volume of the trap column is sufficiently small when compared with the flow rate. Therefore, the influence of the pressure impact is relatively weak, and thus, its influence on the reproducibility of the retention time can be neglected.

Furthermore, the appropriate rotation angles for a six-way valve are 30 degrees and 60 degrees. However, the rotation angle of the rotor is not limited herein, but other rotation angles applicable for the valves of other forms, such as an eight-way valve, also can be employed.

INDUSTRIAL AVAILABILITY

The present invention is applicable for the HPLC for separating and analyzing various compounds in the sample, and the analytical method thereof.

What is claimed is:

1. A flow path switching valve, fitted for a high performance liquid chromatography (HPLC) comprising a trap column, a condensation infusion pump, a sample injection portion, an analytical column and an analysis infusion pump, for switching ports connected to rotor slots by rotating a rotor on which a plurality of the rotor slots is formed, wherein one of the rotor slots is a long rotor slot with a length sufficient for connecting three ports at the same time, and the rotor is interchanged between one position, at which the long rotor slot connects three ports respectively of the trap column, the analysis infusion pump and the analytical column, and another position, at which the long rotor slot connects merely two ports respectively of the trap column and the analysis infusion pump or respectively of the analysis infusion pump and the analytical column, wherein the trap column, the analysis infusion pump and the analytical column are connected and a pressure difference between the trap column and the analytical column is eliminated, when the long rotor slot connects the three ports respectively of the trap column, the analysis infusion pump and the analytical column.

2. The flow path switching valve of claim 1, wherein the long rotor slot has a shape of an arc with a central angle of about 120 degrees.

3. A high performance liquid chromatography (HPLC), comprising: a trap column, for condensing a sample; an condensation infusion pump, for feeding a mobile phase liquid used for condensation into the trap column; a sample injection portion, disposed on a flow path between the condensation infusion pump and the trap column, for injecting the sample into the mobile phase liquid; an analytical column, for separating ingredients of the sample; an analysis infusion pump, for feeding the ingredients already condensed in the trap column into the analytical column by using a mobile phase used for an analysis; and a detector, for detecting the ingredients separated and dissolved by the analytical column, wherein the trap column, the analysis infusion pump, and the analytical column are arranged adjacent to one another, wherein the trap column, the analysis infusion pump, and the analytical column are connected with three ports of the flow path switching valve as claimed in claim 1, and the port of the trap column and the port of the analytical column are respectively located on two sides of the port of the analysis infusion pump; and by means of a rotation of the rotor, a connection among the trap column, the analysis infusion pump, and the analytical column, or a connection of the analysis infusion pump and the trap column, or a connection among the analyzing infusion pump and the analytical column is achieved by the long rotor slot.

4. An analytical method of an HPLC, wherein the HPLC as claimed in claim 3 is adopted, and the analytical method comprises:

(A) a condensation procedure, wherein a rotation angle of the rotor is served as an angle at which the flow path from the sample injection portion is connected to the trap column, so that the sample is led into the trap column, and the ingredients in the sample are condensed;

(B) a high-pressure procedure, wherein the rotation angle of the rotor is served as an angle at which the trap column, the analysis infusion pump, and the analytical column are connected through the long rotor slot, so as to eliminate a pressure difference between the trap column and the analytical column;

(C) a dissolution procedure, wherein the rotation angle of the rotor is served as an angle at which the analysis infusion pump is connected to the trap column through the long rotor slot, and the trap column is connected to the analytical column through other rotor slots, so as to dissolve the ingredients already condensed in the trap column;

(D) a separation procedure, wherein the rotation angle of the rotor is served as an angle at which the analysis infusion pump is connected to the analytical column, and the ingredients already dissolved from the trap column are separated by the analytical column; and (E) a detection procedure, wherein the ingredients dissolved from the analytical column are detected by a detector.

5. The HPLC as claimed in claim 3, wherein the analysis infusion pump is arranged adjacent to the trap column and the analytical column in a manner of connecting concurrently, through the long rotor slot, the port of the analysis infusion pump to both the port of the trap column and the port of the analytical column.

6. The HPLC as claimed in claim 3, wherein the analysis infusion pump is used to feed liquid at a pressure that is higher than that in the condensation infusion pump.

7. An analytical method of an HPLC, wherein the HPLC as claimed in claim 6 is adopted, and the analytical method comprises:

(A) a condensation procedure, wherein a rotation angle of the rotor is served as an angle at which the flow path from the sample injection portion is connected to the trap column, so that the sample is led into the trap column, and the ingredients in the sample are condensed;

(B) a high-pressure procedure, wherein the rotation angle of the rotor is served as an angle at which the trap column, the analysis infusion pump, and the analytical column are connected through the long rotor slot, so as to eliminate a pressure difference between the trap column and the analytical column;

(C) a dissolution procedure, wherein the rotation angle of the rotor is served as an angle at which the analysis infusion pump is connected to the trap column through the long rotor slot, and the trap column is connected to the analytical column through other rotor slots, so as to dissolve the ingredients already condensed in the trap column;

(D) a separation procedure, wherein the rotation angle of the rotor is served as an angle at which the analysis infusion pump is connected to the analytical column, and the ingredients already dissolved from the trap column are separated by the analytical column; and (E) a detection procedure, wherein the ingredients dissolved from the analytical column are detected by a detector.

* * * * *